United States Patent [19]

Poulouse

[11] Patent Number: 5,352,594
[45] Date of Patent: Oct. 4, 1994

[54] SELECTION AND METHOD OF MAKING ENZYMES FOR PERHYDROLYSIS SYSTEM AND FOR ALTERING SUBSTRATE SPECIFICITY, SPECIFIC ACTIVITY AND CATALYTIC EFFICIENCY

[75] Inventor: Ayrookaran J. Poulouse, San Bruno, Calif.

[73] Assignee: Genecor, Inc., Rochester, N.Y.

[21] Appl. No.: 908,596

[22] Filed: Jun. 30, 1992

Related U.S. Application Data

[63] Continuation of Ser. No. 668,311, Mar. 11, 1991, abandoned, which is a continuation of Ser. No. 287,316, Dec. 19, 1988, abandoned, which is a continuation-in-part of Ser. No. 86,869, Aug. 21, 1987, abandoned, which is a continuation-in-part of Ser. No. 905,363, Sep. 9, 1986, abandoned, which is a continuation-in-part of Ser. No. 858,594, Apr. 30, 1986, abandoned, which is a continuation-in-part of Ser. No. 614,612, May 29, 1984, Pat. No. 4,760,025, and a continuation-in-part of Ser. No. 614,615, May 29, 1984, abandoned, and a continuation-in-part of Ser. No. 614,617, May 29, 1984, abandoned, and a continuation-in-part of Ser. No. 614,491, May 29, 1984, abandoned.

[51] Int. Cl.$^5$ .............. C12N 15/10; C12N 15/55; C12N 15/00; C12N 9/20
[52] U.S. Cl. ................. 435/172.1; 435/69.1; 435/198; 435/172.3; 435/874; 435/877; 935/10; 536/23.2
[58] Field of Search .......... 435/195, 196, 197, 198, 435/69.1, 172.1, 172.3, 874, 877; 935/10; 536/23.2

[56] References Cited

U.S. PATENT DOCUMENTS

| | | | |
|---|---|---|---|
| 3,974,082 | 8/1976 | Weyn | 252/95 |
| 4,760,025 | 7/1988 | Estell et al. | 435/222 |
| 4,981,611 | 1/1991 | Kolattukudy et al. | 252/550 |
| 5,030,240 | 7/1991 | Wiersema et al. | 8/111 |
| 5,108,457 | 4/1992 | Poulose et al. | 8/111 |

OTHER PUBLICATIONS

Jordan, F. et al., "Proton Nuclear Magnetic Resonance . . . Thiolsubtilisins", *Biochemistry*, vol. 20, pp. 6366–6370, 1981.

Wright, C. S. et al., "Structure of Subtilisin BPN' at 2.5 Å Resolution," *Nature*, vol. 221, pp. 235–242, 1969.

Winter, G. et al., "Redesigning Enzyme Structure . . . ," *Nature*, vol. 299, pp. 235–242, 1969.

Rasketter, W. H., "Enzyme engineering: Applications and promise," *Trends in Biotech.*, vol. 1, pp. 80–84, 1983.

Robertus, J. D., "An X-Ray Crystallographic Study of the Binding . . . BPN'", *Biochemistry*, vol. 11, No. 13, pp. 2439–2449, 1972.

Köller, W. et al. "Mechanism of Action of Cutinase: Chemical Modification of the Catalytic Triad Characteristic for Serine Hydrolases," *Biochemistry*, vol. 21, pp. 3083–3090, 1982.

Nedkov, P. et al., "Die Primärstruktur von Subtilisin DY", *Hoppe-Seyler's Z. Physiol. Chem.*, bd 364, pp. 1537–1540, 1983.

Svendsen, I., "Chemical Modifications of the Subtilisins with Special Reference to the binding of Large Substrates. A Review", *Carlsberg Res. Sommun*, vol. 41, pp. 237–291, 1976.

Glaser, A., "Transesterification Reactions Catalyzed by Subtilisins," *J. Biol. Chemistry*, vol. 241, pp. 635–638, 1966.

J. E. Fulton et al. "The Glycerol Ester Hydrolase from Corynebacterium acnes: A Serine Hydrolase" Biochemistry 13(11) 2320–2327 (1974).

(List continued on next page.)

*Primary Examiner*—Robert A. Wax
*Assistant Examiner*—Rebecca Prouty
*Attorney, Agent, or Firm*—Margaret A. Horn

[57] ABSTRACT

The invention relates to methods of making and selecting esterase enzymes having an improved perhydrolysis to hydrolysis ratio, and varying $K_{cat}$, $K_m$, and $K_{cat}/K_m$ and substrate specificity. Such enzymes are useful in peracid bleaching systems and other applications.

11 Claims, No Drawings

OTHER PUBLICATIONS

A. Atev. et al. "Isolation of Candida lipolytica mutants with Increased Lipase Activity" Chemical Abstracts. 87:212 Ab. #50085.

W. Kugimiya et al. "Molecular Cloning and Nucleotide Sequence of the Lipase Gene from *Pseudomonas fragi.*" Biochem. Biophys. Res. Commun. 141:185–190 (Nov. 1986).

F. Gotz et al. "Complete Nucleotide Sequence of the Lipase Gene from Staphlococcus . . . " Nuc. Acids Res. 13(16) 5895–5906 (Aug. 1985).

A. J. P. Docherty et al. "Molecular Cloning and Nucleotide Sequence of the Rat Lingual lipose cDNA" Nuc. Acids. Res. 13(6) 1891–1903 (Mar. 1985).

J. McLean et a. "Cloning and Expression of Human Lecithin–Cholesterol Acyltransferase cDNA". Proc. Natl. Acad. Sci. 83:2335–2339 (Apr. 1986).

SELECTION AND METHOD OF MAKING ENZYMES FOR PERHYDROLYSIS SYSTEM AND FOR ALTERING SUBSTRATE SPECIFICITY, SPECIFIC ACTIVITY AND CATALYTIC EFFICIENCY

CROSS REFERENCE TO RELATED APPLICATIONS

This application is a continuation of U.S. patent application Ser. No. 07/668,311, filed Mar. 11, 1991, now abandoned, which is a continuation of U.S. patent application Ser. No. 07/287,316, filed Dec. 19, 1988, now abandoned, which is a continuation in part of U.S. patent application Ser. No. 07/086,869, filed Aug. 21, 1987, now abandoned, which is a continuation in part of U.S. patent application Ser. No. 06/905,363, filed Sep. 9, 1986, now abandoned, which is a continuation in part of U.S. patent application Ser. No. 06/858,594, filed Apr. 30, 1986, now abandoned, which is a continuation in part of U.S. patent application Ser. Nos. 06/614,612, now U.S. Pat. No. 4,760,025, 06/614,615, now abandoned, 06/614,617, now abandoned, and 06/614,491, now abandoned, all filed on May 29, 1984. Cross reference is made to U.S. Ser. No. 872,252 filed Nov. 19, 1986. Cross reference is also made to U.S. patent application Ser. No. 07/705,052, filed May 23, 1991, which is a continuation-in-part of U.S. patent application Ser. No. 629,308, filed Dec. 18, 1990 (abandoned), which is a continuation-in-part of U.S. patent application Ser. No. 465,534, filed Jan. 17, 1990 (abandoned), which is a continuation of U.S. patent application Ser. No. 107,902, filed Oct. 19, 1987 (abandoned), which is a continuation-in-part of U.S. patent application Ser. No. 932,959, filed Nov. 19, 1986 (abandoned).

BACKGROUND OF THE INVENTION a) Field of the Invention

The present invention relates to a method for modifying esterase enzymes with catalytic triads to vary $K_{cat}$, $K_m$ and $K_{cat}/K_m$. It also relates to a method of varying the perhydrolysis/hydrolysis ratio of these enzymes especially for use in bleaching systems. It also relates to modification of the substrate specificity of esterase enzymes.

b) Background Information

A wide variety of esterase enzymes with catalytic site amino acids and in particular catalytic triads are well known. These include serine hydrolases and cystiene hydrolases. Broadly, these enzymes include esterases such as proteases, lipases, phospholipases, carboxyl esterases, wax esterases, cutinases and thio esterases.

These enzymes all act on esters participating in one of two reactions as follows:

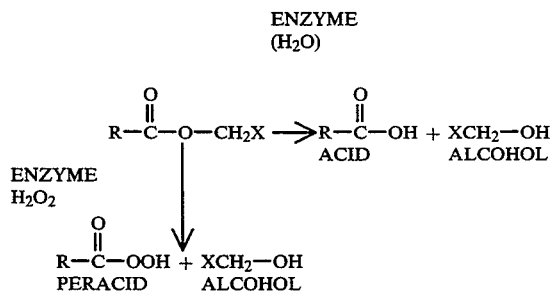

These two types of reactions, perhydrolysis or hydrolysis are competing reactions and any given enzyme with the catalytic triad will produce both peracid and acid if the environment has both a water nucleophile source and a peroxygen nucleophile source. The ratio of these rates for any single enzyme is the perhydrolysis/hydrolysis ratio. These same enzymes also exhibit a given $K_{cat}$, $K_m$ and $K_{cat}/K_m$. These are all measures of the kinetic properties of the enzyme and relate to such functions as substrate specificity and catalytic efficiency.

Substrate Specificity is a ubiquitous feature of biological macro molecules that is determined by chemical forces including hydrogen bonding, electrostatic, hydropholic and steric interactions for a given substrate and measured for a given substrate by Kcat/km and will range from substrate to substrate for a given enzyme. Jencks, W. P., in *Catalysis in Chemistry and Enzymology* (McGraw-Hill, 1969) pp. 321–436; Fersht, A., in *Enzyme Structure and Mechanism* (Freeman, San Francisco, 1977) pp. 226–287. Substrate specificity study of enzymes has been limited to the traditional means of probing the relative importance of those binding forces. Although substrate analogs can be synthesized chemically, the production of modified enzyme analogs has been limited to chemically modified enzyme derivatives (*Ann, Rev. Biochem*, 54, 565–595 (1985) or naturally occurring mutants (*Ann, Rev. Biochem*, 46, 331–358).

Perhydrolysis is useful, among other things, in bleaching systems where the perhydrolysis reaction releases a peracid which is useful for fabric bleaching. European patent application 87-304963.9 describes such a method using an esterase and a peroxygen source to produce peracid for bleaching use. The enzymes described have catalytic triads, i.e. 3 catalytic site amino acids. The reaction is limited by the degree of the competing hydrolysis reaction with water and the enzyme to produce an acid.

Kcat/Km is a measure of the catalytic efficiency of an enzyme with a specific substrate. An enzyme will have a different substrate specificity for each substrate. It is desirable to have an enzyme with a greater (numerically large) $K_{cat}/K_m$ for a given substrate to enable the use of the enzyme more efficiently on the target substrate.

Esterase Enzymes with catalytic triads and catalytic site amino acids are well known and available from a wide variety of sources such as from microbial, plant, insect or animal. These have a variety of useful properties as well as a variety of perhydrolysis/hydrolysis ratios and $K_{cat}$, $K_m$ and $K_{cat}/K_m$ values.

It would be useful if these enzymes could be modified to alter their perhydrolysis/hydrolysis ratio and $K_{cat}$ and $K_m$ so as to be more efficient in a desired reaction (e.g. altered substrate specificity). It would particularly be useful to convert carboxylic acid esters (triglycerides) into peracids by use of an enzyme wherein the competing acid producing reaction is minimized thus leading to a more efficient consumption of substrate.

SUMMARY OF THE INVENTION

It is an object of this invention to provide a method of altering enzymes with catalytic site amino acids, particularly catalytic triads so as to alter their perhydrolysis/hydrolysis ratio and/or $K_{cat}$, $K_m$ and $K_{cat}/K_m$.

It is another object of the invention to provide enzymes made by the method of the invention. It is yet another object of the invention to provide an improved method for production of peracid by action of an enzyme.

Accordingly, the invention provides methods of altering the perhydrolysis/hydrolysis ratio and/or $K_{cat}$, $K_m$ and $K_{cat}/K_m$ of an esterase with a catalytic triad comprising:
a) Selecting an esterase enzyme with a catalytic amino acid; and
b) Replacing an amino acid in the selected enzyme within 15 angstroms from one of the catalytic amino acid sites with an amino acid different than originally occurring in the selected enzyme.

The invention also relates to an in situ generation of peracid and methods of bleaching using an esterase enzyme with one or more catalytic site amino acids, preferably a catalytic triad and a modified esterase with an amino acid within 15 angstroms of a catalytic site amino acid or the catalytic triad replaced with an amino acid different from the one occurring in the same enzyme found in nature and which enzyme has a perhydrolysis/hydrolysis ratio greater than the enzyme found in nature, a substrate which is a functionalized ester of the formula:

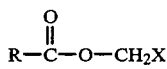

Wherein "R" is a substituent comprising at least one carbon atom and "X" is a functional moiety, the substrate being capable of hydrolysis enzyme and substrate to produce a peracid.

DETAILED DESCRIPTION OF THE INVENTION

Applicants have demonstrated that various methods can be used to produce enzymes with altered perhydrolysis/hydrolysis ratio and $K_{cat}$, $K_m$ and $K_{cat}/K_m$.

Perhydrolysis/hydrolysis ratio relates to the relationship between the rate of production of peracid to the rate of production of acid by an enzyme on a substrate in the presence of water and a peroxygen source. The rates may be determined by any convenient method. For example as in the method in the examples which follow or any other method such as disclosed in European Patent Application No. 87-304963.9. Mutant enzymes with increased or decreased ratios are described in the examples.

A change in substrate specificity is defined as a difference between $K_{cat}/K_m$ ratio of the precursor enzyme and that of the enzyme mutant for a given substrate. A specific enzyme substrate specificity will vary depending upon the substrate selected. The substrate specificity is determined by the comparison of catalytic efficiency for the different substrates. Enzyme mutants with increased or diminished substrate specificity for a given substrate compared to another are described in the example. Generally, the objective will be to produce a mutant having a greater (numerically large) ratio for a given substrate, thereby enabling the use of the enzyme to a more efficient production of peracid or other target result on a target substrate. A substantial change in substrate specificity is preferably at least a twofold increase or decrease. However, smaller increases or decreases in the ratio are also desirable. An increase in $K_{cat}/K_m$ for one substrate may be accompanied by a reduction in another substrate. $K_{cat}/K_m$ may be measured by methods known in the art. For example, as described in EPO application 0130756, specific activity is the product formed per unit of protein per unit time.

a) Selection of an enzyme with catalytic amino acids.

Enzymes of the invention are those enzymes having catalytic site amino acids or catalytic triads such as serine and cystiene hydrolases which catalyze reactions at selected sites in the presence of a nucleophile. They generally catalyze the hydrolysis of ester and amide bends. The substrate (e.g. carboxylic acid ester) reacts with a catalytic amino acid such as serine or cystiene of a serine or cystiene hydrolase to give an intermediate in which the active site oxygen or sulfur forms an ester linkage (acyl enzyme) with the acid group of the substrate. During hydrolysis, water, acting as a nucleophile, attacks the acyl enzyme to give free acid and enzyme. Nucleophiles such as peroxygen sources (hydrogen peroxide, perborate, percarbonate) or other nucleophiles such as alcohols, amines, thiols, etc., can also attack the acyl enzyme yielding a peracid product or esters, amides, thioesters, etc., instead of free acids. In general, serine and cystiene hydrolases catalyze attack by water in preference to other nucleophiles. Selection of enzymes is made depending on the specificity of the enzyme by the particular ester or nucleophile as well as general considerations of availability, cost, safety, etc., known to one skilled in the art. The preferred enzymes are the serine and cystiene hydrolases. Serine and cystiene hydrolases can be selected from groups such as esterases comprising proteases, lipases, phospholipases, etc. See also, *Enzymatic Nomenclature* (1979), pg. 234–274 and 352–355 for a further list of esterases. Examples of suitable proteases include papain, cathepsin, bromelain, chymotrypsin, and subtilisin. Preferred proteases are the subtilisins, especially Subtilisin BPN'. Examples of lipases include animal lipases such as pancreatic, lipoprotein, hepatic, lingual, etc; microbial lipases such as lipases from *Pseudomonas fragi, Pseudomonas fluorescens, Pseudomonas mendocina, Chromobacterium viscosum, Staphylococcus aureus, Candida lipolytica, Geotrichum candidum, Penicillium roqueforti, Aspergillus flavus, Aspergillus niger, Aspergillus oryzae, Rhizopus oligosporus, Rhizopus delemar, Rhizopus arrhizus, Mucor javanicus, Torulopsis ernobii, Penicillium cyclopium, Candida cylindracea, Candida paralipolytica, Leptospira pomona, Leptospira biflexa, Coryebacterium acne*. Preferred esterases are those from Bacillus species such as *B. subtilis*, and include enzymes such as subtilisin BPN', subtilisin Carlsberg, and the like. Lipases for use in the invention also include lipases from other sources such as *Ricinas communis, Veronia anthelmintica, Locusta migatoria, Periplanteta americana, Phiosamia ricini,* and *Diatraea grandiosella*. A most preferred lipase is that enzyme isolated from *Pseudomonas mendocina* ATCC 53552 which has been reclassified as *Pseudomonas mendocino* ATCC 53552. The enzyme has the following amino acid sequence:

```
01            10            20            30
A P L P D T P G A P F P A V A N F D R S G P Y T T S S Q S E G P S C R I Y R P R
41            50            60            70
D L G Q G G V R H P V I L W G N G T G A G P S T Y A G L L S H W A S H G F V V A
```

```
80              90              100             110
A A E T S N A G T G R E M L A C L D Y L V R E N D T P Y G T Y S G K L N T G R V
121             130             140             150
G T S G H S Q G G G G S I M A G Q D T R V R T T A P I Q P Y T L G L G H D S A S
161             170             180             190
Q R R Q Q G P M F L M S G G G D T I A F P Y L N A Q P V Y R R A N V P V F W G E
201             210             220             230
R R Y V S H F E P V G S G G A Y R G P S T A W F R F Q L M D D Q D A R A T F Y G
241             250             260             270
A Q C S L C T S L L W S V E R R G L
```

Methods for producing and purifying such lipase enzyme from *Pseudomonas mendocino* are described in commonly-assigned U.S. application Ser. No. 07/705,052, filed May 23, 1991, the disclosure of which is incorporated herein by reference. Other enzymes with catalytic site amino acids or catalytic triads can readily be identified by one skilled in the art (e.g. see examples). It is anticipated that as new enzymes are discovered with catalytic amino acids that these too will be within the teaching of the present invention.

b) Identification of the site of catalytic amino acids.

The active site of an enzyme such as a serine and cystiene hydrolase is made up of all the catalytic amino acids of the molecule. In the case of enzymes with catalytic triads, the active site comprises three amino acids—aspartic acid, histidine, and (serine or cystiene), in serine and cystiene hydrolases. One of the catalytic amino acids of the active site reacts with the substrate carbonyl to give the acyl enzyme which can then break down either through attack by water (hydrolysis) or attack by a different nucleophile such as peroxygen. See *Enzymatic Reaction Mechanisms*, by C. Walsh, Freeman & Co., 1979 for a discussion of catalytic triad. The catalytic triad can be identified from the crystal structure or by chemical methods (see Means, G., and Feeny, R., *Chemical Modification of Proteins*, Holden-Day, Inc.) and/or by genetic engineering methods. In *Pseudomonas mendocina* (e.g. ATCC 53552) lipase, the catalytic triad amino acids are Ser126, His206, and Asp176 (See descriptions).

c) Selection of the Codon for Replacement.

It has been surprisingly discovered that replacement of an amino acid within about 15 angstroms of an active site of an enzyme will lead to an increase or decrease in perhydrolysis/hydrolysis ratio and $K_{cat}$, $K_m$ and $K_{cat}/K_m$. Replacement of an amino acid greater than about 15 angstroms from the active site has little or no effect on the perhydrolysis/hydrolysis ratio or $K_{cat}$, $K_m$ or $K_{cat}/K_m$.

Enzymes have numerous folds and bends in the structure and one would in general use the crystal structure of the enzyme to determine which am/no acids are within 15 angstroms of the active site regardless of the primary structure of the enzyme. Where no crystal structure is available, positions in the primary sequence about 6 amino acids on either side of a catalytic amino acid would be within the 15 angstrom requirement.

d) Replacement of the Selected Amino Acid.

Once a site is selected within the considerations of the invention, the amino acid may be replaced by any other amino acid usually other than the naturally occurring amino acid, using standard site directed mutagenesis techniques. While it is not possible to predict if the substitution will lead to an increase or decrease in the ratio, Applicant has discovered that either an increase or decrease will occur. Preferred substitutions include the substitutions in subtilisin and equivalent sites around the catalytic serine 221 including positions 222 and 217 in subtilisin. See U.S. patent Ser. No. 614,612 filed May 29, 1984, incorporated herein by reference and substitutions in lipase at positions around two of the amino acids of the catalytic triad at Ser 126 (or Cys 126) and his 206. The replacement may also be made by cassette mutagenesis to facilitate the making of a plurality of mutations. Using this known method, a portion of the DNA corresponding to the 15 angstroms is removed and randomly mutagenized and then replaced.

e) screening.

To determine to what degree and which way the enzyme is modified, the enzyme is screened and compared to values prior to the mutation. The exact method will depend on the exact enzyme reaction being conducted and which nucleophiles are desired. In the peracid generation systems, this consists of measuring the amount of perhydrolysis product and hydrolysis product under a set of fixed conditions both prior and after the mutation of the enzyme using a selected nucleophile such as $H_2O_2$. One skilled in the art would be able to suitably select a method for so doing or could use the procedure used in the examples noted (substituting appropriate reagents, conditions, enzymes, etc.). The screen could consist of any ester as stock substrate in a reaction mix containing any nucleophile or nucleophiles of interest that the operator(s) would like to see substituted for $H_2O$.

f) Repetition of the Mutations

In order to obtain a mutant enzyme with the best ratio or substrate specificity possible in the desired direction, more than one amino acid substitution at a given selected site in the enzyme can be made and the values compared. All nineteen amino acid substitutions could be made to determine which ratio will best suit the users needs. Further, substitutions at more than one site within the parameters of the invention can be done in order to further optimize the results. As stated before, however, no mutations outside the 15 angstrom range will produce a significant effect on perhydrolysis/hydrolysis ratio or substrate specificity. Further, care must be made to preserve the active site function. For example, substitution by non-hydroxyl or non-sulfhydroxyl-containing amino acids at the catalytic serine will inactivate the enzyme entirely.

The enzymes made thus are useful catalysts in perhydrolysis reactions, hydrolysis reactions, and for specific synthesis reactions. Where one desires primarily one type of reaction an enzyme may be selected which favors the desired reaction when compared with the starting enzyme. It should be observed, however, that since only a limited number of substitutions may be made at the selected locations, and as such it is possible, however unlikely, that the starting enzyme will have the desired or maximum result. The method does assure that the ratio or nucleophile specificity may be changed in at least one direction.

The following examples are representative of the invention and not intended to be limiting. One skilled in the art would be able to make changes in the methods, procedures, enzymes selected, etc., based on the disclosure herein.

DESCRIPTION OF THE PREFERRED EMBODIMENTS

Site-Directed Mutagenesis

The following is a description of how specific designated base pair changes were made in a lipase gene from ATCC 53552. The catalytic triad (active site) amino acids in the lipase are at Ser or Cys 126, His 206 and Asp 176. The method used is described by Paul Carter (*Biochem J.*, 237, pp. 1-7 (1986)).

The Eco RI-Sph I fragment from pSN tac II containing the entire lipase gene plus the tac II promotor was ligated into an M13 mp 18 vector which had been digested with EcoRI and Sph I. DNA sense strands were prepared and used as mutagenesis templates. A synthetic primer containing the desired mutation coding for the amino acid change was annealed to the single stranded template creating a double stranded region with one or more base pair mismatches. Nucleotides and the necessary enzymes were added in order to create double stranded plasmid from the primer and template. The resulting plasmid was transformed into *E. coli* JM101 and colonies were analyzed for the desired nucleotide changes. The following mutants were created in this way: Ala-126, Cys-126, Tyr-126, and Gln-206.

Cassette Mutagenesis

The following is a description of how specific designated base pair changes were made in the lipase gene that do not result in an amino acid change, but rather create a unique endonuclease restriction site. The method is described by Norris, et al. (*Nucleic Acids Res.*, 11, pp. 5103-5112, 1983) and Wells, et. al. (*Gene*, 34, pp. 315-323), 1985). Site directed mutagenesis was done in order to create two sets of unique restriction sites on either side of the active serine 126. These changes, which did not affect the amino acid sequence, were AatII-Bam HI. Similarly, unique Bst XI-Bam HI sites were created around the active His 206 site. Each of these sets of mutations was done individually, thus creating two different plasmids with unique sites into which a piece of synthetic DNA or cassette carrying the desired amino acid change(s) can be ligated and therefore exchanged for the wild type. Specific base changes were as follows:

Aat II: CACTTC to GACGTC
Bam HI: GGCTCG to GGATCC
BST XI: CGGGTGTTCTGG to CCAGTGTTCTGG
BAM HI: GGTAGC to GGATCC

In order for the mutagenized Bst XI site to be unique for the His 206 cassettes, a Bst XI site at serine 126 had to be eliminated by changing the serine 126 codon from TCC to TCXG.

The plasmid carrying the mutations for the serine cassettes is designated pGCtacII3AB, indicating a pBR322 plasmid carrying the tacII promoter and the lipase gene with the unique Aat II-Bam HI sites. The plasmid for the histidine mutants was designated pUC119tacII3BB, indicating a pUC plasmid carrying the tacII promoter and the lipase gene with the unique Bst XI-Bam HI sites. All mutants with single amino acid changes other than those described above were done in this way. For the generations of random mutants, cassettes containing random base changes were used.

Double mutants were constructed by digesting the plasmid pGC tac II 3AB containing the desired mutation in the amino acid 126 region with Asp 718 and Acc I, and isolating the 300 base pair fragment. A plasmid puc 119 tac II 3BB with the amino acid change in the 206 region was digested with the same restriction endonucleases and the 300 base pair fragment ligated into the resulting vector.

Isolation of Lipase Enzyme

Cells were grown for 20 h. at 37° C. in two tubes of 5 ml LB+carbenicillin (50 g/ml). Cells were spun down at 6000 rpm/min for 8 minutes at 4° C. in a Sorvall RC-5B. Each cell pellet was resuspended in 1 ml of cold 20% sucrose, 10 mM NaPi (filter sterilized), and 100 uL of 0.25M EDTA pH 8.0. The suspension was incubated on ice for 10-15 minutes, and then centrifuged at 6000 rpm/minute for six minutes at 4° C. The supernatant was then assayed for hydrolytic and perhydrolytic activity.

Purification Protocol for Lipase Variants

This is a general protocol that was used to purify the majority of lipase variants. Fermentation broth was centrifuged at four thousand g for twenty minutes. The supernatant was decanted, and the cell paste is frozen to minus seventy degrees centigrade. The cell paste is then thawed, and homogenized in a Waring blender with four volumes of a buffer consisting of 20% sucrose, 10 mM sodium-phosphate, pH 8. After thirty minutes of stirring, polyethyleninimine is added to a final concentration of 0.1%; it is allowed to stir an additional five minutes. The slurry is then centrifuged at four thousand g for twenty minutes. The supernatant is filtered through a 0.22 micron filter; 10 mM sodium-phosphate, pH 8 is added to the supernatant until the conductivity is 2.2 milliohms. The resulting preparation is chromatographed on a sulfoyl-propyl cation exchange resin using 10 mM sodium-phosphate, pH 8. The lipase enzyme is eluted from the resin using 250 mM sodium chloride, 10 mM sodium phosphate, pH 8. At this point, the lipase preparation is greater than ninety-five percent pure, as judged by SDS-PAGE.

LIPASE SCREENING METHOD FOR DETECTING BETTER PERHYDROLASE MUTANTS EXPRESSED IN *E. COLI*

Transformants containing mutagenized DNA were streaked onto 1.2 micron cellulose acetate filters on Luria Agar (LA)+50 ug/ml Carbenicillin plates to obtain approximately 500 colonies per plate (150 mm petri dishes). Wild type controls were dot inoculated on a small area of each plate and the plates were incubated for 20 hrs. at 37° C.

The cellulose acetate filters containing the transformants and wild type controls were then lifted and transferred to fresh LA+Carb plates and stored at 4° C. The plates from which the filters were lifted were screened for lipase perhydrolysis activity by pouring 18 mls. per plate of an agarose overlay containing:

0.8% agarose in 0.4M $NaH_2PO_4$, pH 9.5
0.1% Trioctanoin/0.01% SDS
500 ppm $H_2O_2$
1 mg/ml o-tolidine.

Positive colonies (indicating perhydrolysis) produced a dark yellow color after 2 hrs. of incubation at room temperature and were selected for by comparison with the wild type controls.

Each corresponding positive colony was picked from the original filter and inoculated into a well of a 96-well sterile titertek plate containing 100 ul of LB+50 ug/ml Carbenicillin (one column was inoculated with a wild type control). This plate was grown 6–7 hrs. (or overnight).

Using a 96-pronged plate stamper, an LA+Carb plate with a cellulose acetate filter was inoculated and allowed to grow for 20 hrs. at 37° C. This plate was then rescreened using the overlay procedure described above for selection of the best mutants. Single glycerol stocks were then prepared by picking colonies from the stamped filter and growing in 5 mls LB 6–7 hrs at 37° C. These glycerol stocks are used for larger scale testing.

Measurement of Hydrolytic/Perhydrolytic Activity of Isolated Lipase Enzymes

Assay solutions are prepared as follows:
Solution A: 270 mg 0-phenylenediamine (OPD), 48 mM NaPi pH 9.2, 70% ethanol in a 10 ml final volume. Keep on ice.
Solution B: 40 mg/ml OPD, pH 5.0 in distilled water. Keep solution on ice.
Solution C: 10% Tricaprylin, 40 mM NaPi, pH 8.4, 1% SDS, in a 10 ml final volume. Sonicate emulsion. Keep at room temperature.

Reaction Mixture:
4 ml $H_2O$
500 micro liters Solution B
50 micro liters 5 mM EDTA pH 7.0
100 micro liters 0.4M NaPi pH 8.4
200 micro liters Soln C Using a pH stat titrator (with constant mixing) reaction mixture is titrated to pH 9.0 with 0.1M NaOH in a closed vessel at 25° C. When the solution reaches pH 9.0, 28 micro liter of 30%, $H_2O_2$ is added. After the solution is retitrated to pH 9.0, the enzyme is added. Hydrolysis rate is measured by the amount of sodium hydroxide used to titrate the carboxylic acid generated. Peracid generated by the enzyme is measured by absorbance after the addition of 100 micro liters of the reaction mixture to 200 micro liter aliquots of solution A and incubation for 5 min followed by the addition of 900 micro liter of $CHCl_3$/MeOH 1:1 (v/v). Absorbance of this solution was measured at 458 nm. A standard curve of absorbance at 458 nm with known varying concentrations of peroctanoic acid, was generated under same experimental conditions and used in calculation of the amount of peracid present in each sample. Under these conditions, 2.45 mM peroctanoic acid generated in the reaction mixture will yield one absorbance unit at 458 nm.

IDENTIFICATION OF CATALYTIC TRIAD AMINO ACIDS OF LIPASE

1. Identification of Active Serine:
Active serine identification was done by three methods:
 a) sequence homology;
 b) chemical modification;
 c) substitution of serine with alanine.

Examination of sequences around active serine (Table 1) of "serine hydrolases" revealed that -Gly-X-Ser-X-Gly- sequence is a conserved sequence among many hydrolases. Based on this sequence homology, Ser 126 was proposed to be the active serine of lipase.

Chemical modification of the lipase with an "active serine reagent", diethyl-p-nitrophenyl phosphate, resulted in inactivation of the enzyme. Complete inactivation of the enzyme occurred when one mole of p-nitrophenol released per mole of enzyme suggesting that one serine of the enzyme was modified with this reagent (Table 2).

After modification with diethyl-p-nitrophenyl phosphate, the modified enzyme was digested with trypsin and the tryptic peptide that was modified with diethyl phosphate was isolated by HPLC and sequenced. This showed that the serine that was modified with this active serine reagent was Ser 126 (Table 3). Site specific mutagenesis at position 126, was done to convert Ser to Ala and the Ala 126 mutant enzyme was isolated by techniques described before. Ala 126 mutant was totally inactive. These results confirm that the active serine of this lipase is Ser 126.

TABLE 1

COMPARISON OF "ACTIVE SERINE" PEPTIDES

| Enzyme | Sequence | | | | |
|---|---|---|---|---|---|
| Lipase I | AGTSG H | S | Q | G | GGGS |
| Pancreatic lipase (porcine) | IG H | S | L | G | |
| Trysin (bovine) | DSCQG D | S | G | G | PVVC |
| Chymotrypsin A (bovine) | SSCMG D | S | G | G | PLVC |
| Elastase | SGCQG D | S | G | G | PLHC |
| Thrombin (bovine) | DACEG D | S | G | G | PFVM |
| Streptomyceds greseus-Trypsin like | TCQG D | S | G | G | PMF |
| Protease A-*S. griseusm* | CAEPG D | S | G | G | SL |
| Alpha-lytic protease | CMGRG D | S | G | G | SW |
| Carboxylesterase (bovine) | G E | S | A | G | AES |
| Choline esterase (horse) | FG E | S | A | G | AAS |
| Fatty acid synthetase (goose) | | S | F | G | ACVA |
| Subtilisin-*B. subtilis* | ATLNG T | S | M | A | SPHV |
| Alkaline protease | G T | S | M | A | |
| Plasmin (human) | AG D | S | A | G | GPLV |
| Thioesterase (duck) | FG H | S | F | G | SFV |

TABLE 2

DEPNP MODIFICATION OF LIPASE 1

Reaction Conditions:
0.1 M NaPi pH 8.2
1.8 mM DEPNP
4.2 mg/ml lipase

| umoles PNP Released umoles Lipase | Lipase Activity % |
|---|---|
| -0- | 100 |
| 1.07 | -0- |

TABLE 3

SEQUENCE DATA

```
                          126
T3-DNA/pro                 |
          ValGlyThrSerGlyHisSerGlnGlyGlyGlyGlySer ...

T3* chem
          ValGlyThrSerGlyHisXsrGlnGlyGlyGlyGlySer ...
```
Chemically derivatized serine only seen at cycle 7, no parent Ser detected
This corresponds to modification of Ser 126 by the diethyl-P-pnitrophenol reagent 2. Identification of Histidine Essential for Catalytic Activity:
Each histidine in the lipase except His 125 was converted into glutamine by site specific mutagenesis.

These mutants were screened for lipase activity on tributyrin plates (luria agar plates with 0.1% tributyrin).

Active lipases will generate clearing zones by the hydrolysis of tributyrin. The results of this experiment is given below:

| Mutants | Tributyrin Clearing |
|---------|---------------------|
| Q49 | + |
| Q71 | + |
| Q75 | + |
| Q156 | + |
| Q206 | − |
| Wild Type | + |

DNA sequence of the mutant gene showed that the histidine to glutamine change was made in each case. Q206 mutant was purified and showed that it did not have any hydrolytic activity with p-nitrophenylbutyrate, tributyrin or tricaprylin as substrates. Therefore, His 206 is essential for the catalytic activity of lipase.

3. Identification of Aspartic Acid Essential for Catalytic Activity:

Each aspartic acid residue in the lipase was converted to asparagine by site specific mutagenesis as described before.

These mutants were screened for lipase activity on agar plates containing tributyrin for clearing zones due to the hydrolysis of tributyrin. The result of this experiment is shown below:

| Mutants | Tributyrin Clearing |
|---------|---------------------|
| N5 | + |
| N18 | + |
| N41 | + |
| N98 | + |
| N105 | + |
| N138 | + |
| N157 | + |
| N176 | − |
| N230 | + |
| N231 | − |
| N233 | + |
| Wild Type | + |

DNA sequencing showed that in each case the mutations for asp to asn conversion had occurred in the gene. However, N176 and N231 did not show tributyrin hydrolysis. These mutants were grown in liquid culture and the lipase protein was partially purified and concentrated by methods described before. Lipase activity of protein obtained from these preparations was measured by a more sensitive assay using hydrolysis of [3H] triolein bound to a polyester swatch as an activity assay. Lipase concentrations were determined by enzyme immunoassays.

Activity Assay Procedure:

Ten 0.5 in X 0.5 in polyester swatches, each loaded with 0.4 micro Ci of [3H] triolein (specific activity = 8.85 mCi/mmole.) were incubated in 5.61 ml of 0.1M glycine—NaOH buffer containing 1% bovine serum albumin at 30° C. on a rotating (150 rpm) shaker bath for various time periods with lipase. Radioactivity released into the buffer from the swatches is a measure of the hydrolysis. Control incubations were carried out without enzyme and the radioactivity released were subtracted as background.

| Enzyme | Results: 3H released into the medium (cpm $10^6$/min/mg enzyme) |
|--------|---------------------|
| WT | 7930 |
| N231 | 2460 |
| N176 | 0 |

These results show that conversion of asp 176 to asn results in an enzyme with less than 1% of wild type activity, whereas all other aspartic acid in the molecule when converted to asparagines yielded active enzymes. Therefore, asp 176 is essential for catalytic activity of the enzyme.

The wild type lipase has an active serine (Ser 126) as identified by reaction with classical active serine reagents and sequence homology with other "serine hydrolases". There is also one histidine (His 206) and one aspartic acid (Asp 176) that are essential for catalytic activity in this lipase. These three amino acids (Set, His, Asp) are typical of the catalytic triad of serine hydrolases and are essential for catalytic activity.

ALTERATION IN $K_m$, $K_{cat}$ and $K_{cat}/K_m$ BY SITE SPECIFIC MUTAGENESIS
Kinetic parameters for wt and variant llipases, determined at pH 8.0 using the substrates p-nitro-phenylacetate, -butyrate and -caprylate (PNA, PNB and PNC). PNC was used in combination with Triton X-100 (endconcentration 0.063%) because it is insoluble in water. PNA and PNB were added as solutions in DMSO (endconcentration 2%). Km and Vmax were calculated from initial rates at different substrate concentrations. Conditions; 100 mM NaP, 25° C.

| | P-NITROPHENYL ACETATE | | | P-NITROPHENYL BUTYRATE | | | P-NITROPHENYL CAPRYLATE | | |
|---|---|---|---|---|---|---|---|---|---|
| | $K_m$ ($\mu$M) | $K_{cat}$ ($s^{-1}$) | $K_{cat}/K_m$ ($s^{-1}mM^{-1}$) | $K_m$ ($\mu$M) | $K_{cat}$ ($s^{-1}$) | $K_{cat}/K_m$ ($s^{-1}mM^{-1}$) | $K_m$ ($\mu$M) | $K_{cat}$ ($s^{-1}$) | $K_{cat}/K_m$ ($s^{-1}mM^{-1}$) |
| WILD TYPE | 1500 | 630 | 420 | 63 | 380 | 6032 | 60 | 26 | 433 |
| ASN127 | 410 | 1.9 | 4.6 | 37 | 0.73 | 20 | 31 | 0.41 | 13 |
| ARG127 | 1900 | 26 | 13.7 | 120 | 6.1 | 50.8 | 67 | 2.5 | 37 |
| CYS127 | 900 | 6.3 | 7.0 | 50 | 4 | 80 | 41 | 3.1 | 76 |
| GLU127 | 300 | 2.3 | 7.7 | 35 | 0.83 | 24 | 38 | 0.36 | 9.4 |
| GLY127 | 1200 | 17 | 14 | 37 | 16 | 432 | 67 | 2.2 | 33 |
| LEU127 | 620 | 8.4 | 14 | 12 | 3.4 | 283 | 12 | 1.1 | 92 |
| SER127 | 70 | 2.5 | 36 | 1.7 | 0.58 | 341 | 4 | 0.68 | 170 |
| THR127 | 160 | 1.4 | 8.8 | 3.1 | 0.5 | 161 | 2 | 0.39 | 195 |
| VAL127 | 2200 | 15 | 6.8 | | | | | | |
| CYS126 | 1000 | 2.8 | 2.8 | 63 | 1.2 | 19 | 82 | 0.18 | 2.2 |
| THR205 | 2900 | 830 | 286 | 70 | 160 | 2286 | 80 | 20 | 250 |
| ARG205 | 820 | 250 | 305 | 49 | 200 | 4082 | 58 | 3.1 | 53 |
| GLU205 | 250 | 260 | 1040 | 100 | 1090 | 10900 | 58 | 141 | 2431 |
| LYS205 | 790 | 440 | 557 | 36 | 166 | 4611 | | | |
| ALA205 | 1900 | 270 | 142 | 33 | 140 | 4242 | | | |

-continued

ALTERATION IN $K_m$, $K_{cat}$ and $K_{cat}/K_m$ BY SITE SPECIFIC MUTAGENESIS
Kinetic parameters for wt and variant llipases, determined at pH 8.0 using the substrates
p-nitro-phenylacetate, -butyrate and -caprylate (PNA, PNB and PNC). PNC was used in
combination with Triton X-100 (endconcentration 0.063%) because it is insoluble in water. PNA
and PNB were added as solutions in DMSO (endconcentration 2%). Km and Vmax were calculated
from initial rates at different substrate concentrations. Conditions; 100 mM NaP, 25° C.

|  | P-NITROPHENYL ACETATE | | | P-NITROPHENYL BUTYRATE | | | P-NITROPHENYL CAPRYLATE | | |
| --- | --- | --- | --- | --- | --- | --- | --- | --- | --- |
|  | $K_m$ ($\mu$M) | $K_{cat}$ ($s^{-1}$) | $K_{cat}/K_m$ ($s^{-1}mM^{-1}$) | $K_m$ ($\mu$M) | $K_{cat}$ ($s^{-1}$) | $K_{cat}/K_m$ ($s^{-1}mM^{-1}$) | $K_m$ ($\mu$M) | $K_{cat}$ ($s^{-1}$) | $K_{cat}/K_m$ ($s^{-1}mM^{-1}$) |
| GLN205 |  |  |  | 33 | 95 | 2879 |  |  |  |
| ASN205 |  |  |  | 48 | 130 | 2708 |  |  |  |
| PRO205 |  |  |  | 40 | 37 | 925 |  |  |  |
| ALA207 | 480 | 215 | 448 | 45 | 370 | 8222 | 50 | 7.4 | 148 |
| HIS207 |  |  |  | 130 | 320 | 2462 | 52 | 4.5 | 87 |
| MET207 | 1100 | 670 | 609 | 40 | 375 | 9375 | 85 | 40 | 470 |
| TRP207 | 1100 | 230 | 209 | 68 | 215 | 3162 |  |  |  |
| TYR207 | 1800 | 330 | 183 | 100 | 275 | 2750 | 100 | 28 | 280 |
| ILE207 | 1200 | 540 | 450 | 63 | 224 | 3556 | 50 | 8.9 | 178 |
| GLY207 |  |  |  | 40 | 60 | 1500 |  |  |  |
| VAL207 |  |  |  | 50 | 410 | 8200 |  |  |  |
| THR207 |  |  |  | 75 | 89 | 1187 |  |  |  |
| ASP207 |  |  |  | 1400 | 310 | 221 |  |  |  |
| ASN207 |  |  |  | 160 | 310 | 1938 |  |  |  |
| SER207 |  |  |  | 46 | 200 | 4348 |  |  |  |
| LYS207 |  |  |  | 38 | 280 | 7368 |  |  |  |
| ASN127-ALA207 |  |  |  | 47 | 0.37 | 8 |  |  |  |
| ARG127-ALA207 |  |  |  | 50 | 7.6 | 152 |  |  |  |
| SER127-ALA207 |  |  |  | 2.6 | 2.8 | 1077 |  |  |  |
| THR127-ALA207 |  |  |  | 2 | 0.9 | 450 |  |  |  |

| LIPASE ALTERED SUBSTRATE SPECIFICITY | |
| --- | --- |
| ENZYME/MUTANT | ($K_{cat}/K_m$) p-nitrophenylbutyrate ($K_{cat}/K_m$) p-nitrophenyl caprylate |
| Arg 205 | 77 |
| Ala 207 | 56 |
| His 207 | 28 |
| Met 207 | 20 |
| Ile 207 | 20 |
| Wild Type | 14 |
| Gly 127 | 13 |
| Cys 126 | 9 |
| Thr 205 | 9 |
| Tyr 207 | 10 |
| Glu 205 | 4 |
| Leu 127 | 3 |
| Ser 127 | 2 |
| Asn 127 | 2 |
| Glu 127 | 3 |
| Arg 127 | 1 |
| Cys 127 | 1 |
| Thr 127 | 0.8 |

This table shows that enzyme's preference for butyrate substrate over caprylate is varied 96-fold by single amino acid substitution.

Hydrolysis/Perhydrolysis Ratio and Specific Activity
of Site-Specific Mutants from the Active Histidine Regions.

Reaction Conditions:
TO/SDS: 0.4%/0/04%   Temperature: 25 C.
H202: 700 ppm (active oxygen)   pH: 9.0 (pH stat)
OPD: 4 mg/ml

| ENZYME | CONC UG/ML | UMOLES/10 MIN/ML HYDROLYSIS | PERHYDROLYSIS | SPECIFIC ACTIVITY UMOLES/10 MIN/UG | | H/P |
| --- | --- | --- | --- | --- | --- | --- |
| WT | 0.2 | 1.58 | 0.24 | 7.90 | 1.20 | 7.0 |
|  | 0.4 | 2.32 | 0.26 | 5.80 | 0.65 | 9.0 |
| Lys207 | 0.3 | 1.30 | 0.11 | 4.60 | 0.38 | 12.0 |
|  | 0.6 | 1.89 | 0.19 | 3.40 | 0.34 | 10.0 |
| Val207 | 0.1 | 1.51 | 0.14 | 10.80 | 1.00 | 11.0 |
|  | 0.3 | 2.06 | 0.17 | 7.40 | 0.61 | 12.0 |
| Ile207 | 0.3 | 2.18 | 0.26 | 7.27 | 0.93 | 8.0 |
|  | 0.6 | 3.08 | 0.33 | 5.10 | 0.56 | 9.0 |
| Met207 | 0.3 | 1.20 | 0.11 | 4.14 | 0.39 | 11.0 |
|  | 0.6 | 1.54 | 0.11 | 2.66 | 0.18 | 15.0 |
| Tyr207 | 0.2 | 1.05 | 0.29 | 4.40 | 1.20 | 4.0 |
|  | 0.6 | 1.91 | 0.32 | 3.20 | 0.53 | 6.0 |
| SER207 | 0.4 | 1.63 | 1.82 | 4.10 | 4.55 | 9.0 |
|  | 0.9 | 3.15 | 0.26 | 3.50 | 0.29 | 12.0 |
| Gly207 | 0.5 | 1.84 | 0.19 | 3.68 | 0.37 | 10.0 |
|  | 0.2 | 1.45 | 0.17 | 7.25 | 0.84 | 9.0 |
| Thr207 | 0.6 | 1.73 | 0.39 | 2.88 | 0.65 | 4.0 |
|  | 1.1 | 2.89 | 0.47 | 2.63 | 0.43 | 6.0 |
| Ala207 | 0.1 | 1.16 | 0.17 | 8.90 | 1.29 | 7.0 |
|  | 0.30 | 1.66 | 0.28 | 6.10 | 1.00 | 6.00 |

-continued

Hydrolysis/Perhydrolysis Ratio and Specific Activity of Site-Specific Mutants from the Active Histidine Regions.

Reaction Conditions:
TO/SDS: 0.4%/0/04%  Temperature: 25 C.
H2O2: 700 ppm (active oxygen)  pH: 9.0 (pH stat)
OPD: 4 mg/ml

| ENZYME | CONC UG/ML | UMOLES/10 MIN/ML HYDROLYSIS | PERHYDROLYSIS | SPECIFIC ACTIVITY UMOLES/10 MIN/UG | | H/P |
|---|---|---|---|---|---|---|
| Gly205 | 0.3 | 1.44 | 0.25 | 4.80 | 0.83 | 6.0 |
|  | 0.7 | 2.13 | 0.32 | 3.00 | 0.46 | 7.0 |
| Glu205 | 0.1 | 0.55 | 0.07 | 5.50 | 0.70 | 8.0 |
|  | 0.3 | 0.81 | 0.15 | 2.70 | 0.50 | 6.0 |
|  | 0.6 | 1.76 | 0.22 | 2.90 | 0.36 | 8.0 |
| Ala205 | 0.2 | 0.04 | 0.16 | 0.20 | 0.80 | 8.0 |
|  | 0.4 | 1.83 | 0.24 | 4.58 | 0.61 | 25.0 |
| Arg205 | 0.6 | 1.77 | 0.20 | 2.80 | 0.32 | 9.0 |
| Lys205 | 0.5 | 1.28 | 0.30 | 2.60 | 0.60 | 4.0 |
|  | 0.7 | 1.72 | 0.31 | 2.30 | 0.42 | 6.0 |
|  | 1.0 | 1.87 | 0.32 | 1.90 | 0.32 | 6.0 |
| Pro205 | 0.3 | 0.94 | 0.15 | 3.10 | 0.48 | 6.0 |
|  | 0.6 | 2.46 | 0.29 | 4.10 | 0.48 | 9.0 |
|  | 0.9 | 2.30 | 0.23 | 2.60 | 0.25 | 10.0 |
| Gln205 | 0.5 | 1.53 | 0.32 | 3.06 | 0.64 | 5.0 |
|  | 1.0 | 2.28 | 0.46 | 2.28 | 0.46 | 5.0 |
| Cys205 | 0.3 | 0.81 | 0.20 | 2.80 | 0.70 | 4.0 |
|  | 0.6 | 1.18 | 0.22 | 2.00 | 0.37 | 5.0 |
| Leu205 | 9.7 | 1.10 | 0.08 | 0.11 | 0.01 | 14.0 |
|  | 19.40 | 1.49 | 0.12 | 0.08 | 0.01 | 13.0 |
| Asn205 | 0.27 | 1.22 | 0.28 | 4.52 | 1.04 | 4.00 |
|  | 0.53 | 1.56 | 0.36 | 2.94 | 0.68 | 4.00 |
| Asn205/Thr207 | 0.1 | 1.49 | 0.27 | 18.60 | 3.40 | 6.0 |
|  | 0.2 | 1.57 | 0.31 | 9.80 | 1.95 | 5.0 |
| Gln205/Thr207 | .1 | 1.15 | 0.25 | 11.50 | 2.48 | 5.00 |
|  | 0.30 | 1.82 | 0.32 | 7.28 | 1.27 | 6.00 |

-continued

Hydrolysis/Perhydrolysis Ratio of Mutants from the Active Serine Region

| ENZYME | SPECIFIC ACTIVITY UMOLES/MG/5 MIN HYDROLYSIS | PERHY-DROLYSIS | RATIO HYD/PERHYD | ENZYME | SPECIFIC ACTIVITY UMOLES/MG/5 MIN HYDROLYSIS | PERHY-DROLYSIS | RATIO HYD/PERHYD |
|---|---|---|---|---|---|---|---|
| WT (Gln127) | 2450.00 | 332.00 | 7.00 | Met127 | 26.00 | 7.00 | 3.70 |
|  |  |  |  | Leu127 | 12.00 | 6.00 | 2.00 |
| Lys127 | 1300.00 | 233.00 | 5.60 | Asn127 | 8.00 | 4.00 | 2.00 |
| Arg127 | 46.00 | 19.00 | 2.40 | His127 | 5.00 | 2.00 | 2.50 |
| Ser127 | 18.00 | 10.00 | 1.80 | Val127 | 5.00 | 2.00 | 2.50 |
| Gly127 | 22.00 | 9.00 | 2.40 | Cys127 | 4.00 | 1.00 | 4.00 |
| Thr127 | 14.00 | 8.00 | 1.80 | Glu127 | 2.00 | 0.50 | 4.00 |

Hydrolysis/Perhydrolysis Ratio and Specific Activity of Double Mutants from the Active Serine and Histidine Regions Reaction Conditions:
TO/SDS: 0.4%/0.04%  Temperature: 25 C.
H2O2: 700 ppm (active oxygen)  pH: 9.0 (pH stat)
OPD: 4 mg/ml

| ENZYME | CONC UG/ML | UMOLES/10 MIN/ML HYDROLYSIS | PERHYDROLYSIS | SPECIFIC ACTIVITY UMOLES/10 MIN/UG HYD | PERHYD | H/P |
|---|---|---|---|---|---|---|
| Asn127/Ala207 | 78.6 | 1.39 | 0.38 | 0.02 | 0.01 | 4.0 |
|  | 104.8 | 1.65 | 0.39 | 0.02 | 0.01 | 4.0 |
| Asn127/Ala207 | 13.9 | 1.07 | 0.16 | 0.08 | 0.01 | 7.0 |
|  | 23.2 | 1.61 | 0.33 | 0.07 | 0.01 | 5.0 |
| Ser127/Ala207 | 19.1 | 1.16 | 0.38 | 0.06 | 0.02 | 3.0 |
|  | 38.2 | 1.89 | 0.46 | 0.05 | 0.01 | 4.0 |
| Thr127/Ala207 | 23.7 | 1.14 | 0.35 | 0.05 | 0.02 | 3.0 |
|  | 47.4 | 2.02 | 0.45 | 0.04 | 0.01 | 4.0 |
| Asn127/Gln205 | 36.0 | 0.61 | 0.19 | 0.02 | 0.01 | 3.0 |
|  | 48.0 | 0.61 | 0.26 | 0.01 | 0.01 | 2.0 |
| Ser127/Gln205 | 5.6 | 0.39 | 0.14 | 0.07 | 0.03 | 3.0 |
|  | 11.2 | 0.67 | 0.32 | 0.06 | 0.03 | 2.0 |
|  | 22.3 | 0.93 | 0.46 | 0.04 | 0.02 | 2.0 |
| Ser127/Thr207 | 19.3 | 1.29 | 0.58 | 0.07 | 0.03 | 2.0 |
|  | 38.6 | 1.82 | 0.74 | 0.05 | 0.02 | 2.0 |
| Thr127/Thr207 | 13.5 | 0.52 | 0.25 | 0.04 | 0.02 | 2.0 |
|  | 33.8 | 1.03 | 0.52 | 0.03 | 0.02 | 2.0 |

-continued

| | | | | | | |
|---|---|---|---|---|---|---|
| Ser127/Asn205 | 4.0 | 0.36 | 0.19 | 0.09 | 0.05 | 2.0 |
| | 8.0 | 0.58 | 0.29 | 0.07 | 0.04 | 2.0 |
| Asn127Asn205 | 17.1 | 0.38 | 0.13 | 0.02 | 0.01 | 3.0 |
| | 34.2 | 0.75 | 0.20 | 0.02 | 0.01 | 4.0 |
| Thr127/Asn205 | 9.4 | 0.37 | 0.16 | 0.04 | 0.02 | 2.0 |
| | 18.8 | 0.52 | 0.26 | 0.03 | 0.01 | 2.0 |
| Thr127/Gln205 | 27.0 | 0.50 | 0.33 | 0.02 | 0.01 | 2.0 |
| | 54.0 | 0.90 | 0.47 | 0.02 | 0.01 | 2.0 |
| Asn127/Thr207 | 33.0 | 0.47 | 0.27 | 0.01 | 0.01 | 2.0 |
| | 66.0 | 1.00 | 0.47 | 0.02 | 0.01 | 2.0 |
| Arg127/Asn205 | 5.76 | 0.41 | 0.14 | 0.07 | 0.02 | 3.00 |
| | 11.52 | 0.62 | 0.21 | 0.05 | 0.02 | 3.00 |

Hydrolysis/Perhydrolysis Ratio of Regiospecific Mutations Around Active Histidine Region Reaction Conditions:
TO/SDS: 0.4%/0.04%   Temperature: 25 C.
H2O2: 700 ppm (active oxygen)   pH: 9.0 (pH stat)
OPD: 4 mg/ml

| | | UMOLES/10 MIN/ML | | |
|---|---|---|---|---|
| ENZYME | CONC UG/ML | HYDROLYSIS | PERHYDROLYSIS | H/P |
| LIPASE 1 | 0.28 | 1.24 | 0.172 | 7.00 |
| LIPASE 8 | 0.33 | 1.62 | 0.262 | 6.00 |
| | 0.50 | 1.89 | 0.376 | 5.00 |
| LIPASE 9 | 0.32 | 0.89 | 0.124 | 7.00 |
| LIPASE 40 | 0.21 | 0.98 | 0.136 | 7.00 |
| | 0.42 | 1.93 | 0.214 | 9.00 |
| LIPASE 41 | 0.30 | 1.45 | 0.30 | 5.00 |
| | 0.60 | 2.62 | 0.58 | 5.00 |
| LIPASE 55 | 0.37 | 1.31 | 0.21 | 6.00 |
| | 0.56 | 1.88 | 0.25 | 8.00 |
| LIPASE 65 | 0.12 | 1.18 | 0.14 | 8.00 |
| | 0.15 | 1.47 | 0.17 | 9.00 |
| LIPASE 66 | 0.35 | 2.01 | 0.16 | 13.00 |
| | 0.35 | 1.72 | 0.15 | 12.00 |
| LIPASE 67 | 0.14 | 1.48 | 0.29 | 5.00 |
| | 0.21 | 1.97 | 0.32 | 6.00 |
| LIPASE 68 | 0.13 | 1.67 | 0.25 | 7.00 |
| | 0.10 | 1.32 | 0.18 | 7.00 |
| LIPASE 69 | 0.41 | 1.57 | 0.31 | 5.00 |
| | 0.62 | 2.20 | 0.34 | 6.00 |
| LIPASE 70 | 0.65 | 1.20 | 0.28 | 4.00 |
| | 0.98 | 1.66 | 0.41 | 4.00 |
| LIPASE 14 | 0.06 | 0.47 | PERHYDROLYSIS NOT DETECTABLE | |
| LIPASE 15 | 0.14 | 1.30 | 0.08 | 16.00 |
| LIPASE 60 | 0.01 | 1.54 | PERHYDROLYSIS NOT DETECTABLE | |
| LIPASE 67Q | 0.48 | 2.86 | 0.48 | 6.00 |
| | 0.24 | 1.84 | 0.36 | 5.00 |
| LIPASE 67N | 0.35 | 2.35 | 0.44 | 5.00 |
| | 0.21 | 1.67 | 0.33 | 5.00 |
| LIPASE 67F | 0.18 | 1.72 | 0.27 | 6.00 |
| | 0.30 | 2.10 | 0.31 | 7.00 |
| LIPASE 67M | 0.11 | 2.07 | 0.21 | 10.00 |
| | 0.18 | 2.41 | 0.27 | 9.00 |
| LIPASE 68Q | 0.34 | 3.09 | 0.36 | 9.00 |
| | 0.17 | 1.94 | 0.24 | 8.00 |
| LIPASE 68N | 0.26 | 2.77 | 0.29 | 9.00 |
| | 0.13 | 1.80 | 0.16 | 11.00 |
| LIPASE 68M | 0.21 | 2.45 | 0.24 | 10.00 |
| | 0.42 | 3.33 | 0.37 | 9.00 |
| LIPASE 68P | 0.12 | 2.24 | 0.22 | 10.00 |
| | 0.24 | 3.67 | 0.36 | 10.00 |
| LIPASE 71 | 0.11 | 1.24 | 0.28 | 5.00 |
| | 0.18 | 1.90 | 0.37 | 5.00 |
| LIPASE 72 | 0.10 | 1.21 | 0.22 | 6.00 |
| | 0.20 | 1.97 | 0.39 | 5.00 |
| LIPASE 83 | 0.05 | 0.96 | 0.18 | 5.00 |
| | 0.10 | 1.56 | 0.32 | 5.00 |
| LIPASE 85 | 0.04 | 0.91 | 0.13 | 7.00 |
| | 0.06 | 1.26 | 0.19 | 7.00 |
| LIPASE 88 | 0.08 | 0.86 | 0.12 | 7.00 |
| | 0.14 | 1.06 | 0.16 | 7.00 |
| LIPASE 91 | 0.08 | 0.72 | 0.07 | 11.00 |
| | 0.16 | 0.89 | 0.13 | 7.00 |
| LIPASE 96 | 0.07 | 0.91 | 0.15 | 6.00 |
| | 0.13 | 1.41 | 0.27 | 5.00 |
| LIPASE 99 | 0.07 | 1.01 | 0.17 | 6.00 |
| | 0.11 | 1.23 | 0.19 | 6.00 |
| LIPASE 84 | 0.03 | 1.12 | 0.22 | 5.00 |
| LIPASE 87 | 0.05 | 1.50 | 0.25 | 6.00 |
| | 0.08 | 2.35 | 0.33 | 7.00 |
| LIPASE 86 | 0.03 | 1.19 | PERHYDROLYSIS NOT DETECTABLE | |
| LIPASE 90 | 0.09 | 1.39 | 0.31 | 5.00 |

| | | | | |
|---|---|---|---|---|
| | 0.18 | 2.06 | 0.39 | 5.00 |
| LIPASE 92 | 0.04 | 1.29 | 0.27 | 5.00 |
| | 0.08 | 2.01 | 0.39 | 5.00 |
| LIPASE 94 | 0.17 | 1.17 | 0.22 | 5.00 |
| | 0.34 | 1.73 | 0.34 | 5.00 |
| LIPASE 95 | 0.07 | 1.22 | 0.25 | 5.00 |
| | 0.14 | 2.05 | 0.39 | 5.00 |
| LIPASE 97 | 0.08 | 1.24 | 0.26 | 5.00 |
| | 0.16 | 2.21 | 0.40 | 5.00 |
| LIPASE 100 | 0.07 | 1.29 | 0.27 | 5.00 |
| | 0.14 | 2.10 | 0.38 | 6.00 |
| LIPASE 101 | 0.05 | 1.22 | 0.26 | 5.00 |
| | 0.09 | 1.85 | 0.38 | 5.00 |
| LIPASE 104 | 0.08 | 1.66 | 0.31 | 5.00 |
| | 0.12 | 2.13 | 0.37 | 6.00 |
| LIPASE 105 | 0.12 | 1.48 | 0.29 | 5.00 |
| | 0.25 | 2.40 | 0.40 | 6.00 |
| LIPASE 106 | 0.09 | 1.30 | 0.24 | 5.00 |
| | 0.19 | 1.76 | 0.36 | 5.00 |
| LIPASE 107 | 0.12 | 1.30 | 0.30 | 4.00 |
| | 0.19 | 1.76 | 0.36 | 5.00 |
| LIPASE 108 | 0.13 | 1.10 | 0.14 | 8.00 |
| | 0.26 | 1.69 | 0.23 | 7.00 |
| LIPASE 109 | 0.08 | 0.72 | 0.12 | 6.00 |
| | 0.15 | 1.37 | 0.21 | 6.00 |
| LIPASE 111 | 0.07 | 1.20 | 0.24 | 5.00 |
| | 0.14 | 2.03 | 0.34 | 6.00 |
| LIPASE 114 | 0.44 | 1.07 | 0.18 | 6.00 |
| | 0.87 | 1.54 | 0.32 | 5.00 |
| LIPASE 122 | 0.29 | 0.90 | 0.21 | 4.00 |
| | 0.44 | 1.19 | 0.28 | 4.00 |
| LIPASE 123 | 0.10 | 0.74 | 0.15 | 5.00 |
| | 0.30 | 1.88 | 0.34 | 6.00 |
| LIPASE 124 | 0.13 | 0.73 | 0.16 | 5.00 |
| | 0.30 | 1.70 | 0.33 | 5.00 |
| LIPASE 125 | 0.05 | 0.64 | 0.12 | 5.00 |
| | 0.18 | 1.44 | 0.29 | 5.00 |
| LIPASE 126 | 0.13 | 1.04 | 0.27 | 4.00 |
| | 0.26 | 1.77 | 0.33 | 5.00 |
| LIPASE 127 | 0.08 | 0.95 | 0.16 | 6.00 |
| | 0.17 | 1.33 | 0.28 | 5.00 |
| LIPASE 128 | 0.07 | 0.87 | 0.19 | 5.00 |
| | 0.15 | 1.37 | 0.27 | 5.00 |
| LIPASE 129 | 0.05 | 0.95 | 0.24 | 4.00 |
| | 0.10 | 1.57 | 0.31 | 5.00 |
| LIPASE 130 | 0.08 | 1.13 | 0.24 | 5.00 |
| | 0.17 | 1.77 | 0.34 | 5.00 |
| LIPASE 131 | 0.12 | 1.13 | 0.24 | 5.00 |
| | 0.23 | 1.77 | 0.34 | 5.00 |
| LIPASE 119 | 0.07 | 0.88 | 0.15 | 6.00 |
| | 0.24 | 1.78 | 0.37 | 5.00 |
| LIPASE 132 | 0.20 | 1.83 | 0.40 | 5.00 |
| | 0.63 | 4.04 | 0.51 | 8.00 |
| LIPASE 133 | 0.07 | 1.13 | 0.11 | 11.00 |
| | 0.13 | 1.90 | 0.15 | 12.00 |
| LIPASE 134 | 0.09 | 1.32 | 0.30 | 4.00 |
| | 0.18 | 1.96 | 0.40 | 5.00 |
| LIPASE 84W | 0.19 | 0.37 | 0.33 | 1.00 |
| | 0.37 | 1.22 | 0.48 | 3.00 |
| LIPASE 84X | 0.15 | 0.64 | 0.26 | 2.00 |
| | 0.30 | 1.39 | 0.44 | 3.00 |
| LIPASE 84Y | 0.11 | 0.55 | 0.31 | 2.00 |
| | 0.22 | 1.66 | 0.57 | 3.00 |
| LIPASE 84Z | 0.10 | 0.53 | 0.29 | 2.00 |
| | 0.20 | 1.38 | 0.48 | 3.00 |
| LIPASE 92W | 0.34 | 0.79 | 0.40 | 2.00 |
| | 0.67 | 1.23 | 0.40 | 3.00 |
| LIPASE 92X | 0.14 | 0.27 | 0.30 | 1.00 |
| | 0.28 | 1.57 | 0.43 | 4.00 |
| LIPASE 92Z | 0.15 | 0.97 | 0.29 | 3.00 |
| | 0.30 | 1.50 | 0.40 | 4.00 |
| LIPASE 92Y | 0.15 | 0.87 | 0.26 | 3.00 |
| | 0.30 | 1.46 | 0.36 | 4.00 |

What is claimed is:

1. A method of altering the perhydrolysis/hydrolysis ratio of *Pseudomonas mendocina* lipase ATCC #53552, said lipase characterized in that it comprises a catalytic triad consisting of Ser126, His206 and Asp176, said method comprising:

a) replacing at least one amino acid in said lipase with a different amino acid, at a position within four (4) amino acid residue positions on the amino-terminal side or on the carboxyl-terminal side of Ser126, His206 or Asp176;

b) determining the perhydrolysis/hydrolysis ratio of said lipase of step a); and c) selecting the lipase of step b) characterized in that the perhydrolysis/hydrolysis ratio of the lipase is increased by a factor of at least 2 when compared to native *Pseudomonas mendocina* lipase ATCC #53552.

2. A method of claim 1 wherein the lipase has cutinase activity.

3. A method of claim 1 wherein at least one amino acid is replaced in *Pseudomonas mendocina* lipase ATCC #53552 at a position selected from the group consisting of +127, +205, and +207.

4. A method of altering the substrate specificity of *Pseudomonas mendocina* lipase ATCC #53552, said lipase characterized in that it comprises a catalytic triad consisting of Ser126, His206 and Asp176, said method comprising:

a) replacing at least one amino acid in said lipase with a different amino acid, at a position within four (4) amino acid residue positions on the amino-terminal side or on the carboxyl-terminal side of Ser126, His206 or Asp176;

b) determining the substrate specificity of said lipase of step a); and c) selecting the lipase of step b) characterized in that the substrate specificity of the lipase is increased by a factor of at least 2 when compared to native *Pseudomonas mendocina* lipase ATCC #53552.

5. A method of claim 4 wherein the lipase has cutinase activity.

6. A method of claim 4 wherein at least one amino acid is replaced in *Pseudomonas mendocina* lipase ATCC #53552 at a position selected from the group consisting of +127, +175, +177, +203, +205 and +207.

7. A method of altering the catalytic efficiency of *Pseudomonas mendocina* lipase ATCC #53552, said lipase characterized in that it comprises a catalytic triad consisting of Ser126, His206 and Asp176, said method comprising:

a) replacing at least one amino acid in said lipase with a different amino acid, at a position within four (4) amino acid residue positions on the amino-terminal side or on the carboxyl-terminal side of Ser126, His206 or Asp176;

b) determining the catalytic efficiency of said lipase of step a); and c) selecting the lipase of step b) characterized in that the catalytic efficiency of the lipase is increased by at least 25% when compared to native *Pseudomonas mendocina* lipase ATCC #53552.

8. A method of claim 7 wherein the lipase has cutinase activity.

9. A method of claim 7 wherein at least one amino acid is replaced in *Pseudomonas mendocina* lipase ATCC #53552 at a position selected from the group consisting of +175, +177, +202, +203, +205 and +207.

10. A method of claim 3 wherein at least two amino acids are replaced in *Pseudomonas mendocina* lipase ATCC #53552 at positions selected from the group consisting of +205/+207, +127/+207 and +127/+205.

11. A method of claim 6 wherein at least two amino acids are replaced in *Pseudomonas mendocina* lipase ATCC #53552 at positions +202/+203.

* * * * *